United States Patent [19]
Hori et al.

[11] Patent Number: 5,989,182
[45] Date of Patent: Nov. 23, 1999

[54] DEVICE-STEERING SHAFT ASSEMBLY AND ENDOSCOPE

[75] Inventors: Koichiro Hori, Framingham; Philip R. Lichtman, Newton; David I. Freed, Westboro, all of Mass.

[73] Assignee: Vista Medical Technologies, Inc., Carlsbad, Calif.

[21] Appl. No.: 08/994,537

[22] Filed: Dec. 19, 1997

[51] Int. Cl.⁶ .................................................. A61B 1/05
[52] U.S. Cl. ........................ 600/112; 600/144; 600/173
[58] Field of Search .................... 600/109, 112, 600/173, 164, 140, 143, 144, 150

[56] References Cited

U.S. PATENT DOCUMENTS

| | | | |
|---|---|---|---|
| 3,900,021 | 8/1975 | Makepeace et al. | 600/112 |
| 4,043,323 | 8/1977 | Komiya | 600/104 |
| 4,543,090 | 9/1985 | McCoy | 600/151 |
| 4,611,888 | 9/1986 | Prenovitz et al. | 600/112 |
| 4,753,223 | 6/1988 | Bremer | 600/140 |
| 4,756,313 | 7/1988 | Terwilliger | 600/104 |
| 4,884,557 | 12/1989 | Takehana et al. | 600/151 |
| 5,010,876 | 4/1991 | Henley et al. | 600/112 |
| 5,127,394 | 7/1992 | Lane | 600/112 |
| 5,195,968 | 3/1993 | Lundquist et al. | 604/95 |
| 5,275,152 | 1/1994 | Krauter et al. | 600/140 |
| 5,307,803 | 5/1994 | Matsuura et al. | 600/140 |
| 5,307,804 | 5/1994 | Bonnet | 600/109 |
| 5,512,035 | 4/1996 | Konstorum et al. | 600/149 |
| 5,538,497 | 7/1996 | Hori | 600/182 |
| 5,582,576 | 12/1996 | Hori et al. | 600/173 |
| 5,603,687 | 2/1997 | Hori et al. | 600/166 |
| 5,662,584 | 9/1997 | Hori et al. | 600/103 |
| 5,683,348 | 11/1997 | Diener | 600/143 |
| 5,762,603 | 6/1998 | Thompson | 600/112 |

*Primary Examiner*—Paul J. Hirsch
*Attorney, Agent, or Firm*—Pandiscio & Pandiscio

[57] ABSTRACT

An endoscope is provided that comprises an imaging device such as a micro-size video camera supported by a novel device-steering shaft assembly. The shaft assembly comprises a malleable or rigid shaft, an imaging device carrier releasably and pivotally supporting the imaging device at one end of the shaft, and operating means including a flexible operating cable and cable moving means attached to the opposite end of the shaft for moving said cable and thereby pivoting the imaging device carrier relative to the shaft so as to alter the viewing angle of the supported imaging device. Using a malleable shaft offers the advantage that the shaft is manually reformable into various configurations to facilitate access to different surgical sites, with the shaft having the ability to remain in each selected configuration until manually reformed into another configuration. Alternatively, the imaging device may be permanently attached to the device carrier. A routing configuration for the cable permits the imaging device to be rotated sufficiently to attain retrograde viewing. The endoscope may be converted to another instrument by replacing the imaging device on the device carrier with some other device such as a surgical laser, a magnetic sensor, an infra-red or other radiation sensor, an infra-red or other radiation transmitter, an ultrasonic transducer, or other surgical device such as a surgical scissors or a grasper.

25 Claims, 12 Drawing Sheets

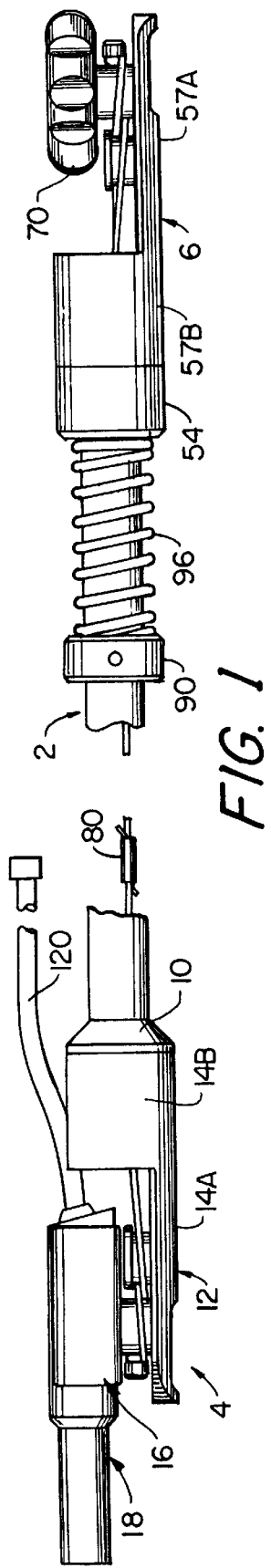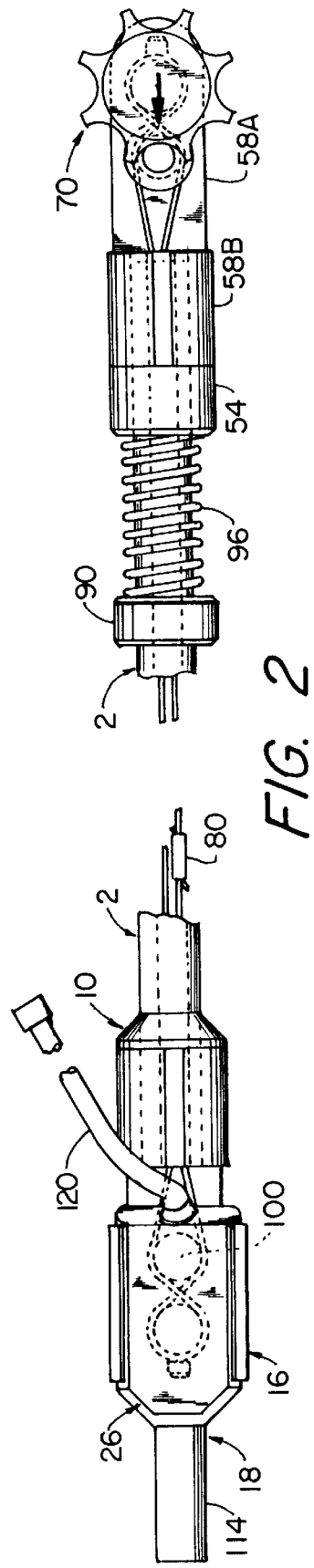

DEVICE-STEERING SHAFT ASSEMBLY AND ENDOSCOPE

BACKGROUND OF THE INVENTION

1. Field of the Invention

This invention relates to device-steering shaft assemblies and instruments embodying same, more particularly to video endoscopes comprising device steering means which allow an operating physician to view surgical sites from different angles.

2. Description of the Prior Art

Endoscopes and borescopes, which are telescopic instruments used to inspect cavities or openings or other selected sites, have found a number of applications in medicine and other technologies. In the field of medicine, the use of endoscopes permits inspection of organs or tissue for the purpose of facilitating the obtainment of biological specimens or the viewing of a surgical site for the purpose of facilitating the manipulation of surgical instruments so as to avoid or minimize invasive and traumatizing surgical procedures.

Endoscopes generally comprise an insertion portion in the form of a tubular shaft that is designed to be inserted into a patient. Older conventional endoscopes used in medicine contain an objective lens unit at the distal (forward) end of the insertion portion which transmits an image of the area forward of the objective lens unit to a remote eyepiece for viewing by the surgeon, the image being transmitted to the eyepiece via an image-forwarding means in the form of a relay lens set, or an optical fiber bundle unit. In more recent years, in place of the eyepiece and at least part of the image forwarding means, it has been preferred to provide a small size solid state electronic video imaging device, such as one employing a CCD chip, in the imaging plane of the objective lens unit, and applying the output of that video imaging device via a suitable electronic transmission system to a video monitor for viewing by a user. The combination of an objective lens unit and a solid state video imaging device constitutes a video camera, and an endoscope that utilizes a video camera is known as a video endoscope. With both types of endoscopes, a surgeon can view the displayed image and use the information conveyed by that image to manipulate the endoscope and also other surgical instruments that have been inserted into the patient via the same or another incision or opening in the patient's body. Video endoscopes also may be of the stereo variety so as to provide depth perception. Stereo video endoscopes comprise optical means for generating first and second optical images, and video imaging means for generating first and second electrical signals in response to the first and second optical images respectively.

The present state of the art of endoscopes prior to this invention is demonstrated by the following U.S. patent applications and patents: (1) copending application Ser. No. 08/722742, filed Oct. 1, 1996 by K. Hori et al; (2) U.S. Pat. No. 5,538,497, issued Jul. 23, 1996 to K. Hori; (3) U.S. Pat. No. 5,582,576, issued Dec. 10, 1996 to K. Hori et al; (4) U.S. Pat. No. 5,603,687, issued Feb. 18, 1997 to K. Hori et al; and (5) U.S. Pat. No. 5,662,584, issued Sep. 2, 1997 to K. Hori et al; and the prior art cited in said application and patents. To the extent necessary, the teachings of those patent applications are incorporated herein by reference thereto.

Originally the insertion portion of endoscopes had a generally rigid tubular construction and the endoscopes looked straight ahead. However, soon variants were developed having fixed angular deviations from straight ahead viewing, typically 30°. Subsequently, endoscopes with flexible tubular insertion portions appeared. Some of these flexible endoscopes can be remotely steered, such as by cables which cause the flexible shaft to bend. However, existing instruments of this type have limited angular deflection capabilities and limited minimum radii of curvature.

In so-called minimally invasive surgery, an endoscope is used to visualize the operating field inside a body cavity while the surgeon manipulates instruments therein so as to perform the surgical procedure.

New recently developed minimally invasive endoscopic procedures, such as thoracoscopy, are making greater demands upon endoscopic orientation than existing instruments can practically provide. For instance, it is becoming necessary to look sideways (i.e., 90°) or even retrograde (approaching 180°). In conjunction with the need for a larger range of viewing angle, there is also the requirement that the tip of the endoscope be positionable within the body cavity so as to take full advantage of the larger range of viewing angle. For instance, if it is desired to view an organ from behind—that is, to extend the endoscope beyond the organ and observe its hidden surfaces in retrograde fashion—then positioning the endoscope for this purpose may be impossible with a rigid, straight shaft endoscope or with currently available flexible shaft endoscopes. It would be helpful to the physician to be able to configure the insertion portion of the endoscope in a manner advantageous for entry and positioning relative to the surgical site, and have the endoscope maintain that configuration until changed by the physician. It also would be of value to be able to vary the orientation of the video camera in different situations without being restricted by the physical construction of the insertion portion. A further consideration of this invention is that many commercially available endoscopes have been designed for particular procedures and are not suitable for use in other procedures.

SUMMARY OF THE INVENTION

A primary object is to provide a device-steering shaft assembly for use with a camera or other device.

Another primary object is to provide a video endoscope having a novel insertion portion characterized by a video camera that is steerable relative to the insertion portion.

Another primary object of the invention is to provide an improved endoscope having a video camera steerably mounted on a malleable shaft which is manually configurable so as to facilitate access to a surgical site and is adapted to retain the selected configuration until manually shaped to another configuration.

Another primary object is to provide an improved endoscope wherein the insertion portion comprises a shaft, a device support member or carrier pivotally mounted to the front end of the shaft, and a camera detachably mounted on the device support member.

Still another object is to provide an endoscope with an imaging system that can be manipulated remotely by a surgeon or other operator so as to view an organ from behind—that is, to extend the endoscope beyond the organ and observe its hidden surfaces in retrograde fashion.

The foregoing and other objects rendered obvious hereinafter are achieved by the present invention which is essentially a device supporting and steering guide (hereafter also identified as "shaft assembly" that comprises a shaft, a device carrier rotatably attached to one end of the shaft with the carrier being capable of being rotated at least 90° right or left from a straight-ahead position, and operating means connected to the shaft that permit an operator to rotate the device carrier remotely, the carrier being adapted to securely support a selected device such as a video camera, sensor, transducer, laser or a surgical instrument for rotation therewith.

In the preferred embodiment of the invention, the selected device is a micro-size video camera that is releasably held by the device carrier, and the combination of device supporting and steering guide and video camera form the insertion portion of a video endoscope. Also in such an endoscope the shaft that supports the device carrier is malleable in the sense that it can be bent by a surgeon to a desired shape and will retain that shape until manually reconfigured to another shape. As an optional and preferred feature the device carrier is adapted to be rotated more than 90° from its normal straight-ahead position, so that in the case of a video endoscope a retrograde viewing capability is provided for the video camera. The video camera is provided with a camera cable comprising electrical wiring for coupling the camera's electronic circuits to a video controller that controls operation of the camera's CCD unit(s) and processes the electrical output of the camera for use in operating an electronic display apparatus so as to cause the latter to display a video reproduction of the image seen by the camera. In the preferred form of endoscope, the camera includes fiber-optic elements for transmitting light to a surgical site viewed by the camera, and the camera cable includes terminal portions of those fiber-optic elements and means for coupling those elements to a light source, whereby to provide light to illuminate a surgical site. The electronic display apparatus may be a video monitor and/or a heads-up display.

The operating means includes first and second support means attached to first and second ends of the shaft, first and second rotatable transverse axles mounted on said first and second support means, respectively, and a flexible but stretch-resistant filament or cable that extends about both axles, with the device carrier attached to the first axle for rotation therewith and the second axle being connected to means for rotating it, whereby rotation of the second axle causes the filament to apply a rotational force to the first axle to change the angular position of the carrier and attached camera or other imaging device. In the case where the shaft of the device-supporting guide is a malleable shaft, a preload mechanism (preferably employing a spring) is incorporated so that when the shaft is bent, thereby changing its axial length in the fashion described as "bend allowance" in the sheet metal-forming industry, the filament or cable does not become slack and in fact maintains a desired tension at all times. The desired tension is such that backlash (hysteresis) is virtually eliminated and there is optimal friction between the axles and the structure that rotatably supports them. Friction is considered optimal when the mechanism has a good tactile feel when the proximal axle is rotated manually, such as by a knob, and the distal axle is resistant to accidental rotation when the device is bumped against some resistant structure or organ.

By combining the malleability of the shaft and the rotatability of the imaging device carrier, the operator can position the imaging or other device wherever he requires it to be, including orienting it in a retrograde fashion back toward the user. In various embodiments the axles' rotational range can be less that one complete turn or as many as several complete turns.

In the case of a video endoscope having a malleable shaft, a surgeon is able to hand-bend the malleable shaft so that, once inserted into a body cavity, the camera will be positioned where it is needed. Next he rotates the camera so that it presents the smallest possible cross-section to the incision through which it will be emplaced, and inserts the camera into the body cavity. Then he rotates the camera remotely so that its optical axis points in the desired direction. Thus an endoscope embodying the invention provides the surgeon three combinable ways to direct the camera device: first, the position of the camera device within the body cavity is adjustable by bending the malleable shaft appropriately; second, the line of sight of the camera is adjustable through the operating means described above; and third, a considerable amount of positional adjustment is available, as is customarily true, by the surgeon's manual manipulation of the instrument.

In an alternate embodiment of the invention, the malleable shaft may be replaced by a rigid shaft that is straight or preformed in a selected curved configuration.

The above and other features of the invention, including various novel details of construction and combinations of parts, will now be more particularly described with reference to the accompanying drawings which illustrate the invention and its use to form a novel video endoscope. The features of the invention and the preferred embodiment herein described are intended by way of illustration only and not as a limitation of the invention. Accordingly it is to be understood that the principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention and from which its novel features and advantages will be apparent.

In the drawings:

FIG. 1 is a fragmentary side elevation view of a video endoscope constituting a preferred embodiment of the invention, the endoscope comprising a malleable shaft supporting a video camera, with the camera pointing straight ahead (distally) and the malleable shaft in an unbent condition;

FIG. 2 is a fragmentary plan view of the endoscope shown in FIG. 1;

In the several figures, identical elements are identified by the same numerals.

DETAILED DESCRIPTION OF THE PREFERRED EMBODIMENT

Figure 3:
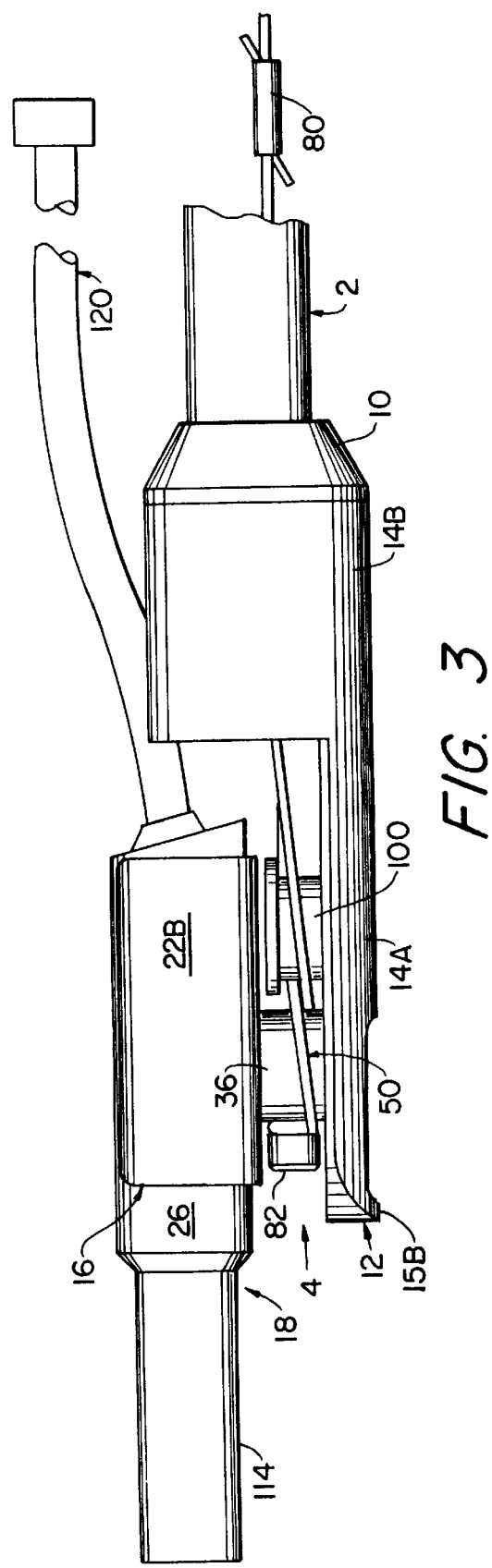
FIG. 3 is an enlarged side elevation view of the distal portion of the apparatus of FIGS. 1 and 2.
Figure 4:
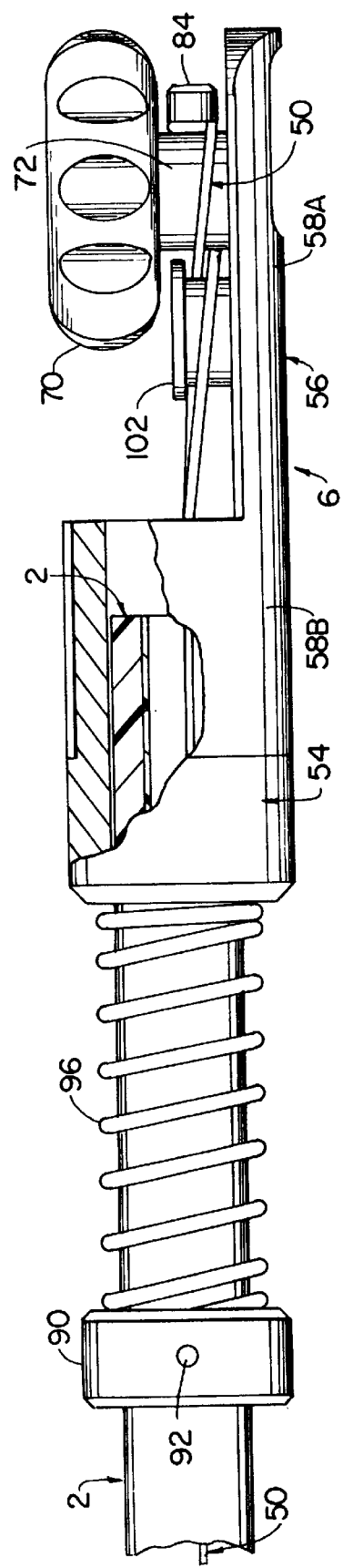
FIG. 4 is an enlarged side elevation view of the proximal portion of the apparatus of FIGS. 1 and 2.

The invention is described hereinafter in the context of its being used to provide a video endoscope, but it is to be understood that a device other than a video camera, e.g., a laser or ultrasonic transducer, may be mounted on the device carrier of the device supporting and steering guide to provide instruments for other purposes.

Referring first to FIGS. 1–9, the illustrated embodiment of the invention includes a device supporting and steering guide or shaft assembly comprising a shaft 2 connecting a front camera support unit or assembly identified generally by the numeral 4 and an actuating mechanism support unit or assembly identified generally by the numeral 6. Shaft 2 may be rigid or stiff, but preferably it is malleable in the sense that it can be bent to a variety of shapes and will remain in a selected shape until it is bent to a different shape. Further details and various forms of shaft 2 are described hereinafter.

The camera support unit 4 comprises a cylindrical adaptor 10 that surrounds and is secured to the distal end of shaft 2, and a camera support member 12 that comprises a first distal (front) portion 14A and a second proximal (rear) portion 14B. Proximal portion 14B is a split cylinder that surrounds and tightly grips adaptor 10 so that support member 12 cannot move relative to the adaptor. Distal portion 14A has a flat surface 15A that extends parallel to the axis of adaptor 10 and a curved outer surface 15B that is an extension of the outer surface of proximal portion 14B. Support member 12 may be made of a metal or a suitable plastic, e.g., stainless steel, aluminum, polypropylene, high density polyethylene, or a glass fiber reinforced plastic.

Figure 12:
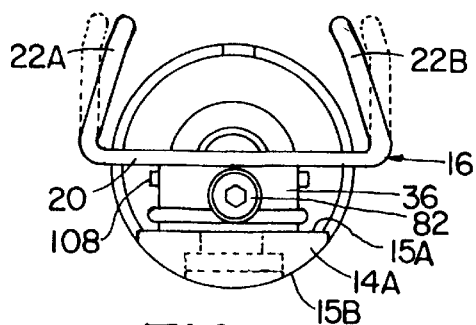
FIG. 12 is a front view of the invention with the imaging device carrier pointing straight ahead.
Figure 13:
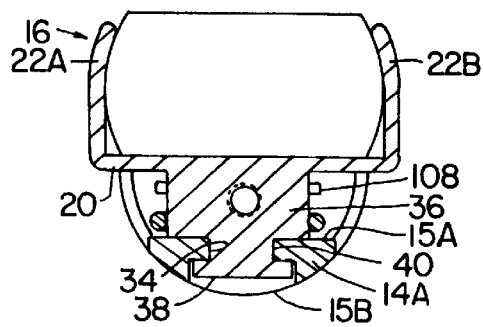
FIG. 13 is a cross-sectional view of the imaging device carrier taken through the center of its pivot shaft.

As seen best in FIGS. 1–3, 5, 7, 9, 10, 12 and 13, camera support unit 4 also comprises a camera carrier or mounting means 16 that supports a camera 18 having a housing 26. Carrier 16 is characterized by a flat bottom wall portion 20 and a pair of oppositely-disposed side wall portions 22A and 22B. Preferably carrier 16 is formed so that side wall portions 22A and 22B are inclined in mutually converging relation, as seen in FIGS. 12 and 13. Carrier 16 preferably is made of metal, but also may be molded of a suitable plastic. In either case, its side wall portions 22A and 22B are spring-like in the sense that they will return to their as-formed position and shape if deflected and then released.

As explained further hereinafter, camera 18 is a monocular or stereo video camera. Essentially a video camera comprises an objective lens system for transmitting monocular or stereo images and an electronic imaging means in the form of one or more CCD's or like solid state devices, such cameras being illustrated and described, for example, in U.S. Pat. Nos. 4,873,572, 4,862,873, 4,873,572, 5,582,576, and 5,832,003, and copending U.S. patent application Ser. No. 08/722,742, filed Oct. 1, 1996 by Koichiro Hori et al. The type and form of the camera is not critical to this invention, except that its housing must be adapted to be releasably mounted to camera carrier 16.

Preferably but not necessarily, camera housing 26 has a cylindrical distal extension 114 that houses the optics portion (not shown) of the camera, while the housing contains the solid state electronic imaging means (also not shown).

Further by way of example regarding stereo cameras, the housing 26 may contain two solid state imaging devices (not shown) disposed side by side. Also the optics contained in distal extension 114 may consist of two objective lens units mounted side by side so that each provides a separate image of the viewed area in front of the camera. Alternatively the camera may comprise a single objective lens mounted in tubular extension 114 that is designed so as to be capable of providing two separate stereo images. Stereo arrangements that employ two objective lenses are shown by Wood et al, "Stereoendoscopy Gives Surgeons Normal Vision", Photonics Spectra, pp. 40–43, Sept. 1993, and by U.S. Pat. Nos. 4,873,572 and 4,862,873. The single objective lens stereo arrangement also is well known, being shown, for example, by U.S. Pat. Nos. 5,122,650 and 5,191,203, both issued to Harry R. McKinley.

Further in the case where the housing 26 serves to contain two video imaging devices, e.g., two CCD units (not shown), the two imaging devices are arranged so that one receives a first one of the two optical stereo images and the other receives the second of the two optical stereo images. The two imaging devices produce first and second electrical signals representative of the first and second received images respectively.

Referring now to FIGS. 1 and 2, housing 26 has a generally rectangular cross-sectional shape, and carrier 16 is sized so that the normal minimal distance between its side wall portions 22A and 22B (FIG. 12) is less than the maximum side-to-side dimension of housing 26. Consequently carrier or mount 16 accepts housing 26 only by forcing apart side wall portions 22A and 22B, with the result that the camera is secured to the clip mount by a tight, releasable friction grip.

Referring now to FIGS. 1, 3, 5, 7 and 9, carrier 16 is pivotally mounted to the front (distal) portion 14A of camera support member 12. For this purpose, the distal portion 14A is formed with a keyhole shaped hole which, as seen best in FIGS. 5, 7 and 9, comprises an enlarged circularly curved section 30 and an elongate smaller section 32 that is circularly curved at the end thereof opposite to the circular section 30. Additionally, the underside of portion 14A is undercut so as to form a thin lip 34 surrounding the smaller opening section 32.

The bottom wall 20 of camera carrier 16 is provided with a cylindrical projection 36 which serves as an axle or pivot shaft for the carrier (and also as the driven spindle or pulley for cable 50). The latter has a reduced diameter extension 38 (FIG. 7) with a peripheral groove 40, the width of groove 40 being sized so as to accommodate lip 34 of the keyhole 30, 32 with a clearance just enough to allow relative rotation of the shaft. The diameter of the reduced diameter extension 38 is slightly smaller than the diameter of the large section 30 of the keyhole opening, but greater than the diameter of the smaller section 32 of the same keyhole opening. As a consequence, the reduced diameter end extension 38 of pivot shaft 36 can be inserted in the larger section 30 of the keyhole opening and then the pivot shaft can be moved laterally (i.e., lengthwise of shaft 2) so that the lip 34 extends into peripheral groove 40, in the manner shown in FIGS. 7, 9 and 13. As a consequence, camera carrier axle 36 can rotate on its own axis while being captivated against movement along its own axis by engagement of lip 34 with the reduced diameter section 38.

As already stated, shaft 2 may be a rigid or stiff member, but preferably it is a malleable member as hereinafter described in greater detail. Regardless of its form it must be constructed so as to provide a passageway for a flexible operating cable or filament as shown at 50 that is used to effect rotation of camera carrier 16 as hereinafter described. In the preferred embodiment, shaft 2 is characterized by a single lumen which is lined with a cylindrical liner 48 (FIG. 14) and serves as a passageway for operating cable 50.

Turning now to FIGS. 1, 2, 4 and 6, actuating mechanism support unit or assembly 6 on the proximal end of shaft 2 also functions as a handle for manually grasping the endoscope. Support 6 comprises an adaptor in the form of cylindrical sleeve 54 which surrounds and makes a close sliding fit with shaft 2, and a proximal support member 56 that is substantially identical to camera support member 12. Hence support member 56 has a proximal (rear) portion 58A and a distal (front) portion 58B. The latter portion is a split cylinder that surrounds and tightly grips sleeve 54 so that support member 56 cannot move relative to that sleeve. Proximal portion 58A has a flat surface 57A that extends parallel to the axis of sleeve 54 and a curved outer surface 57B that is an extension of the outer surface of distal portion 58B. The proximal portion 58A of support member 56 is formed with a keyhole shaped hole (FIG. 6) that is similar to the keyhole 30, 32 of camera support member 12 previously described, this second keyhole shaped opening comprising a large circularly curved section 62 and an elongate smaller section 64 that is circularly curved at its end opposite section 62. The underside of proximal portion 58 is undercut around keyhole section 64, so as to provide a thin lip 68 similar to lip 34. The purpose of keyhole 62, 64 is to facilitate attachment of an operating wheel or knob 70. The latter is provided on one side with a directional marker 71 (shown as an arrow), and on its opposite side it is provided with a cylindrical projection 72 that functions as an axle or pivot shaft for the knob (and also as a drive spindle or drive pulley for cable 50). Axle 72 has the same diameter as axle 36. Axle 72 has a reduced diameter end section 74 and a peripheral groove 76. The diameter of reduced diameter section 74 is slightly smaller than the diameter of the larger keyhole section 62, but greater than the diameter of the smaller keyhole section 64. As a consequence, the reduced diameter end section 74 of shaft 72 can be inserted in the larger keyhole section 62 and then shifted laterally (i.e., lengthwise of sleeve 54) into the smaller diameter keyhole section 64, so that lip 68 extends into groove 76. As a further consequence, axle 72 can rotate on its axis relative to flat portion 58A but is restrained by lip 68 against movement along its own axis so long as it occupies smaller keyhole opening 64.

Operating cable 50 is preferably a flexible stainless steel woven filament which, although it has a small diameter, preferably between 0.25 and 0.40 mm for an endoscope having a maximum outside diameter ("o.d.") of about 10 mm., is resistant to stretching. However, the cable could be made of other materials possessing like characteristics. The ends of cable 50 are joined to one another. The ends may be joined in various ways, e.g., by welding or by a conventional crimp-type cable connector 80 as shown at 80 in FIGS. 1 and 2.

Figure 5:
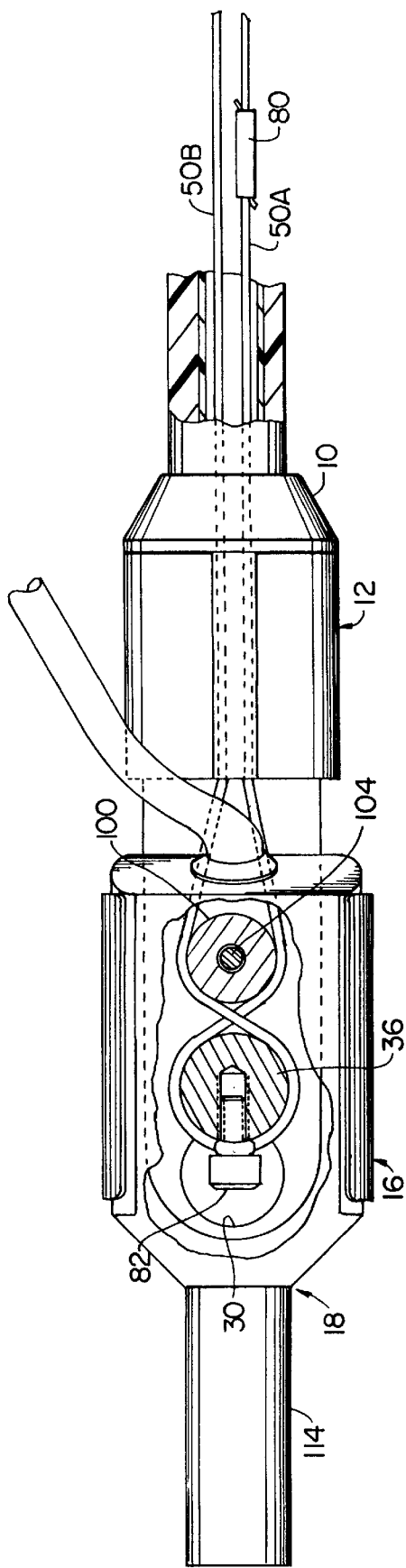
FIG. 5 is an enlarged plan view of the distal portion of the same apparatus, with certain components shown in section.
Figure 6:
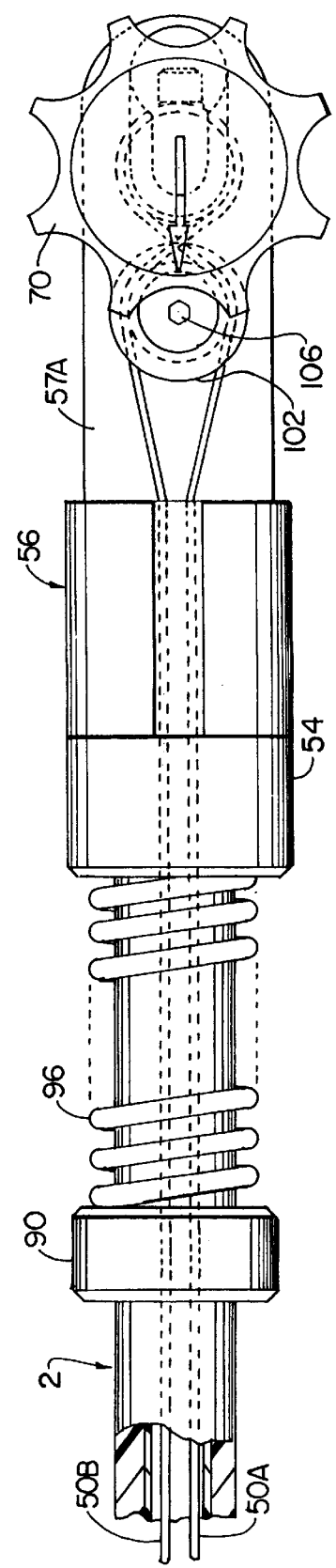
FIG. 6 is an enlarged plan view of the proximal portion of the same apparatus.
Figure 7:
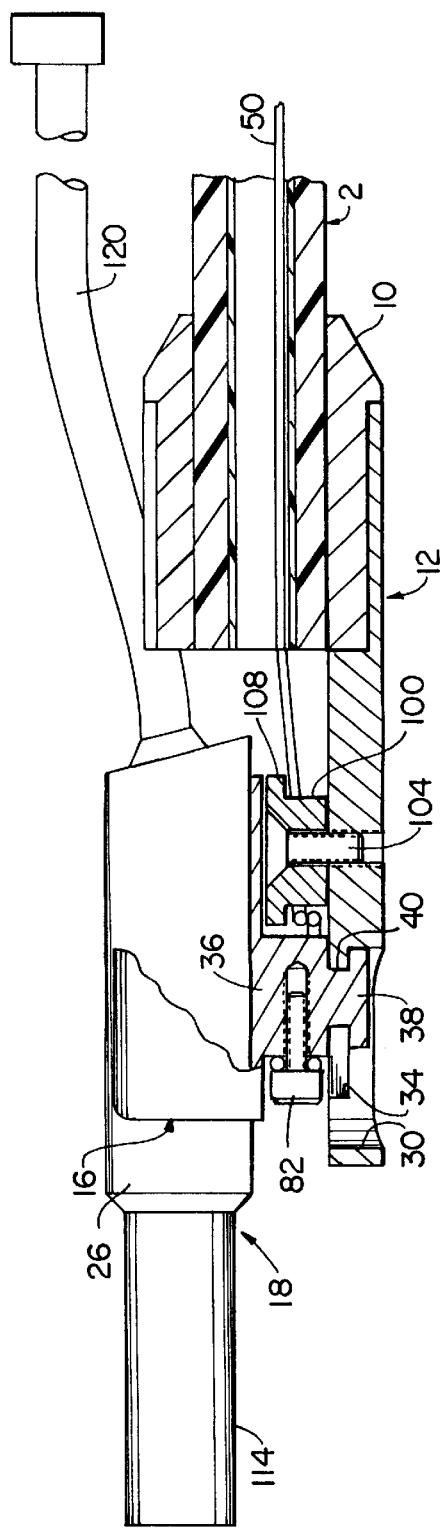
FIG. 7 is a view like FIG. 3, but with certain parts shown in section so as to illustrate certain features in greater detail.
Figure 15:
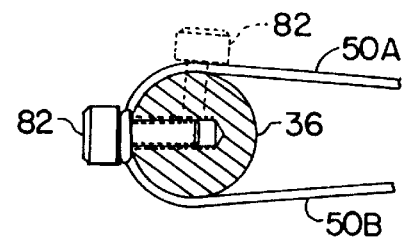
FIG. 15 is a transverse cross-sectional view of the axle portion of the imaging device carrier of FIG. 1.
Figure 17:
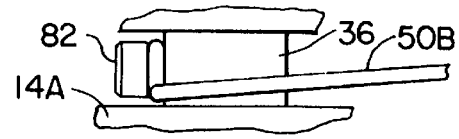
FIG. 17 is a partial side elevation of the axle portion of the imaging device carrier shown in FIG. 15.

Cable 50 passes around and is secured to the cylindrical axle or pivot shaft 36 of camera carrier 16. Preferably this is accomplished by mounting a screw 82 in a radially-extending blind hole in axle 36. As seen in FIGS. 5, 15 and 17, the cable is wrapped around the shank of screw 82 and is locked against movement relative to the axle by virtue of being clamped to the shaft by the head of the screw. Of course, cable 50 could be secured to axle 36 by some other means in place of screw 82. The cable is secured to axle 36 for the purpose of preventing any slippage between the cable and the axle when a pulling force is exerted on the cable for the purpose of effecting rotation of the axle.

Cable 50 also passes around and is secured to axle or pivot shaft 72 of wheel 70. Preferably this is accomplished by mounting another screw 84 (FIGS. 4 and 8) in a blind radially-extending hole in axle 72. The cable is wrapped around the shank of screw 84 and is locked in place by the force exerted by the head of the screw on axle. Essentially the portion of the cable that is wrapped around the shank of screw 84 is clamped to axle 72 by the head of the screw, so that the cable cannot move relative to the wheel 70. Of course, cable 50 could be secured to pivot shaft (axle) 72 by some other means in place of screw 84. It should be noted that the opposite ends of operating cable 50 could be joined together by locking them both to axle 36 by screw 82 (or to axle 72 by screw 84).

As seen in FIGS. 1–18, imaging device carrier 16 and wheel 70 are retained rotatably by imaging device support member 12 and proximal support member 56 respectively by the cooperation of axles 36 and 72 with features of the keyhole shaped openings 30, 32 and 62,64 under the influence of tension in cable 50. The process of assembling the apparatus involves inserting shaft 36 though the large keyhole section 30 and then sliding it laterally (i.e., lengthwise of support member 12) so that its groove 40 is mated with lip 34, whereby axle 36 can rotate but is retained by lip 34. The same procedure is used to rotatably secure axle 72 of wheel 70 to the operating mechanism support member 56.

In this connection it should be noted that according to one embodiment of the invention wherein shaft 2 is rigid or stiff and in a straight or curved configuration, adaptor sleeve 54 may be locked to shaft 2 by crimping or some other means (e.g., by a cement, brazing, welding, or the like depending on the materials of which the various components are made), in which case cable 50 is sized or arranged so as to be under a tension that is adequate to cause shafts 36 and 72 to be held in the smaller diameter sections 32 and 64 of the two keyhole shaped openings, whereby lips 34 and 68 will keep the two shafts engaged with the two support members 12 and 56.

However, locking sleeve 54 to shaft 2 is not acceptable if shaft 2 is malleable, due to the need to maintain tension as the shaft is bent by the operator into a desired configuration. Therefore, if shaft 2 is malleable, sleeve 54 is required to be adjustable lengthwise on shaft 2. Consequently if operating cable 50 should for any reason tend to become slack, its tension can be restored simply by sliding proximal adapter sleeve 54, and hence proximal support member 56, in a proximal direction.

In the preferred embodiment illustrated in FIGS. 1–14, this tensioning is rendered automatic by virtue of a collar 90 and a compression spring 96. Collar 90 is secured to shaft 2, preferably by means of a pin 92. Alternatively collar 90 could be secured to shaft 2 by crimping or other suitable means, e.g., by a cement or by welding or brazing, depending on the materials involved. Compression spring 96 loosely surrounds shaft 2 between collar 90 and the distal face of adaptor sleeve 54. Spring 96 is sized so that at all times it is compressed between collar 90 and sleeve 54 and urges that sleeve to slide proximally on shaft 2 away from collar 90 and distal adaptor 10, thereby maintaining tension on operating cable 50. If for any reason tension in operating cable 50 is reduced, said tension is restored automatically by the force exerted by spring 96. For instance, if shaft 2 is malleable and the operator elects to bend it in one or more places to provided a desired curved configuration, there may result a change of path of operating cable 50 due to its tendency to follow the inside radii of the bends, and such change of path might result in a change of tension in operating cable 50, the consequence being that the pointing direction of imaging device 4 no longer faithfully reflects the pointing direction of directional marker 71.

Directional marker 71 on operating knob 70 is rigidly phased (by operating cable 50) to the direction in which imaging device carrier 16 is pointing. Since axles 36 and 72 are of equal diameter, and since operating cable 50 is locked to both axles, is under tension and is substantially immune to stretching, the phase relationship between imaging device carrier 16 and operating knob 70 is tightly controlled. That is to say, when operating knob 70 is turned in either direction, the resulting rotation of axle 72 causes cable 50 to rotate axle 36 and thereby imaging device carrier 16 in the same direction and by the same magnitude.

Figure 10:
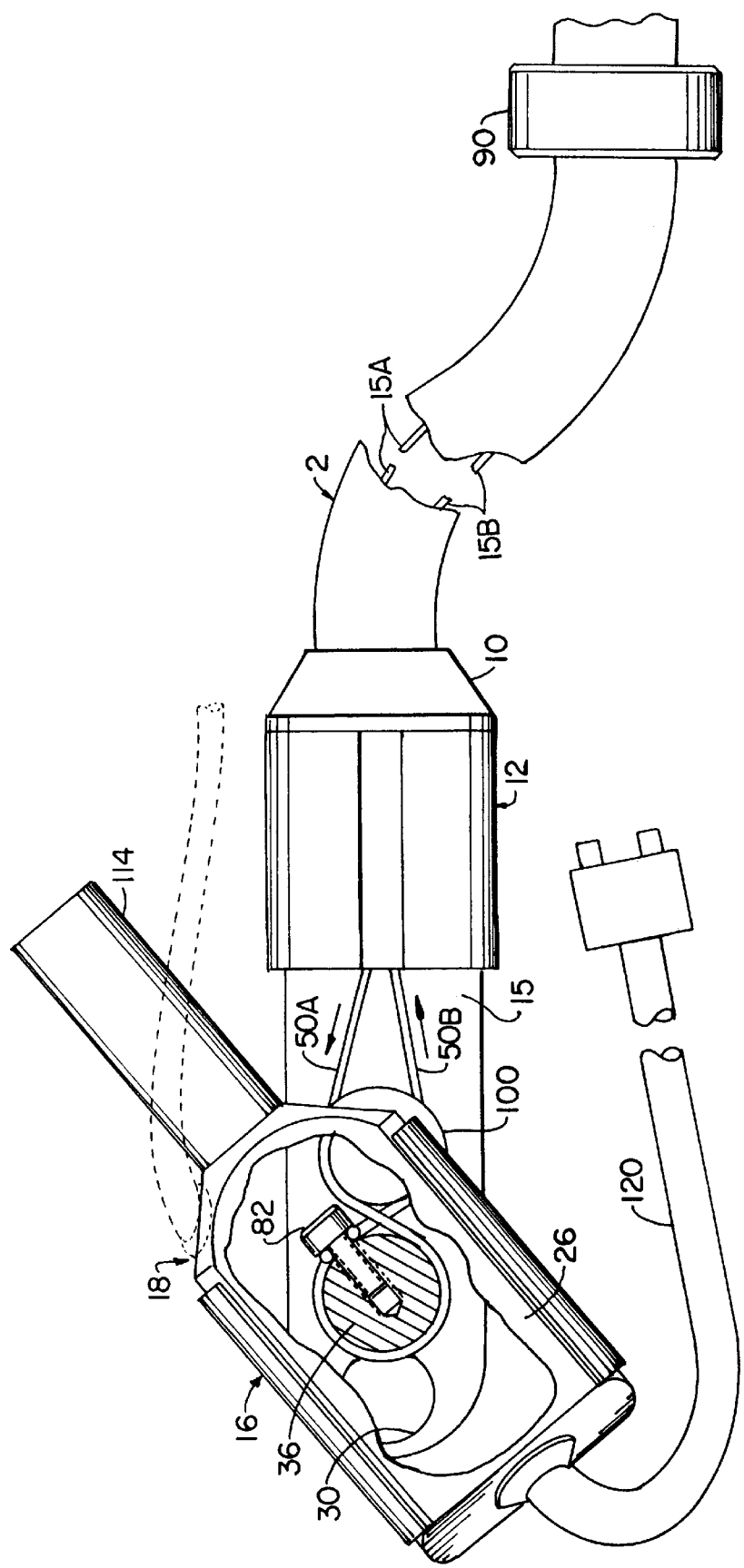
FIG. 10 is a fragmentary plan view of the distal end of the same apparatus with the camera rotated through a substantial angle.
Figure 11:
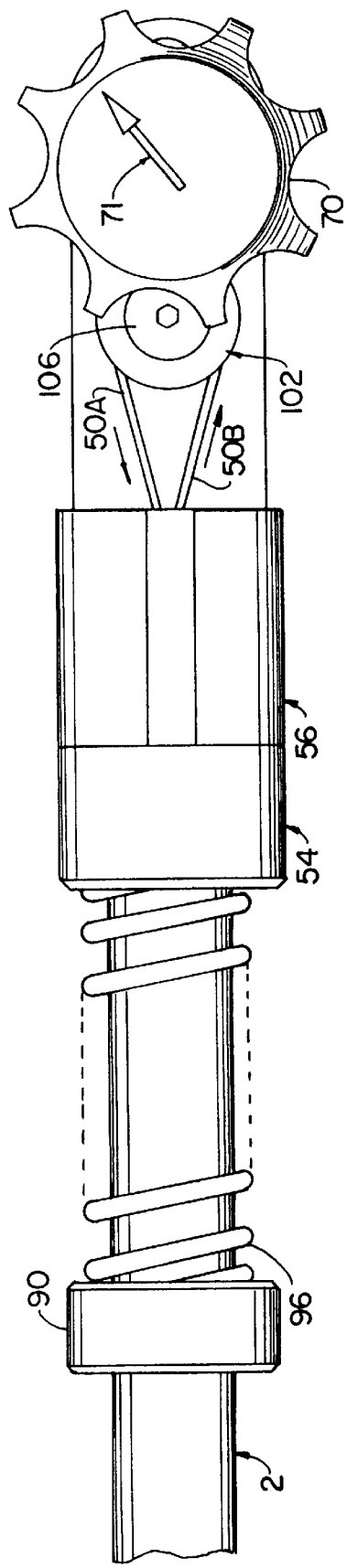
FIG. 11 is a fragmentary plan view of the proximal end of the same apparatus showing the position of the directional member when the imaging device is in the position shown in FIG. 10.

Referring to FIG. 2 wherein shaft 2 is straight, it is seen that imaging device 18 is directed straight ahead, i.e. in line with shaft 2 and pointing away from the operator end of the endoscope, and directional marker 71 also is pointing directly away from the operator and in line with shaft 2. In essence the pointing directions of directional marker 71 and imaging device 18 are defined with respect to the axis of shaft 2 immediately adjacent to sleeve 54 and adaptor 10 respectively. The action of spring 96 maintains the desired tension in operating cable 50 so that when shaft 2 is bent, even to a very pronounced bent shape such as is depicted in FIG. 10, the pointing directions (as defined above) of imaging device 18 and directional marker 71 of knob 16 are the same with respect to the axis of shaft 2 immediately adjacent to sleeve 54 and adaptor 10 respectively. For example, if imaging device 18 is turned 300 to the right relative to the axis of adaptor 10, marker 71 will also be pointing 300 to the right with respect to the axis of sleeve 54. Thus, knowing the shape and disposition of the malleable shaft in a patient, by observing the position of marker 71 the operator is able to point imaging device 18 precisely as he desires to do.

The automatically-operating cable tensioning feature of the invention also compensates for loss of tension resulting from thermal expansion differences between operating cable 50 and shaft 2, or from any other cause. For this reason, it also is preferred to utilize the cable tensioning capability provided by the combination of slidable sleeve 54, spring 96 and collar 90 even when the shaft 2 is rigid or stiff.

Figure 8:
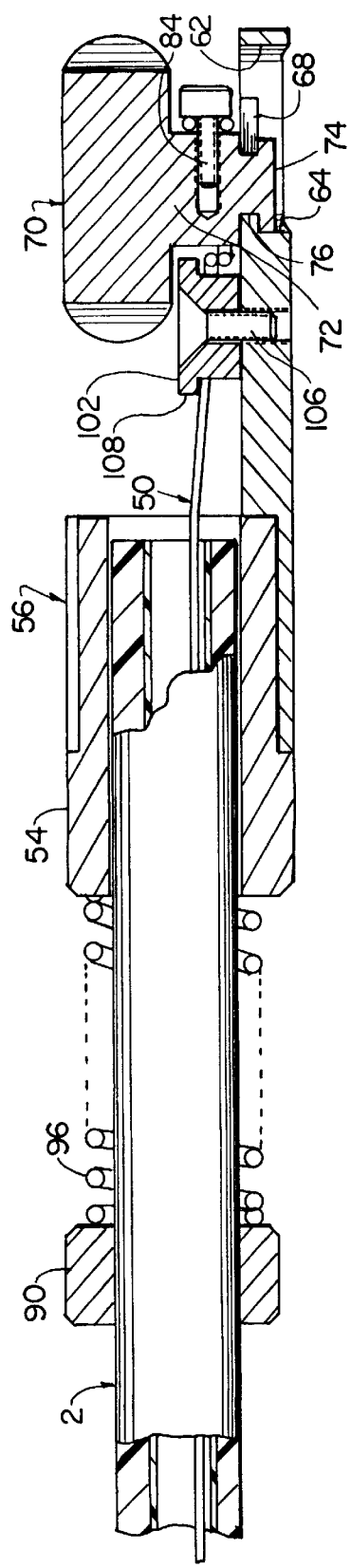
FIG. 8 is a view like FIG. 4, but with certain parts shown in section so as to illustrate certain features in greater detail.
Figure 9:
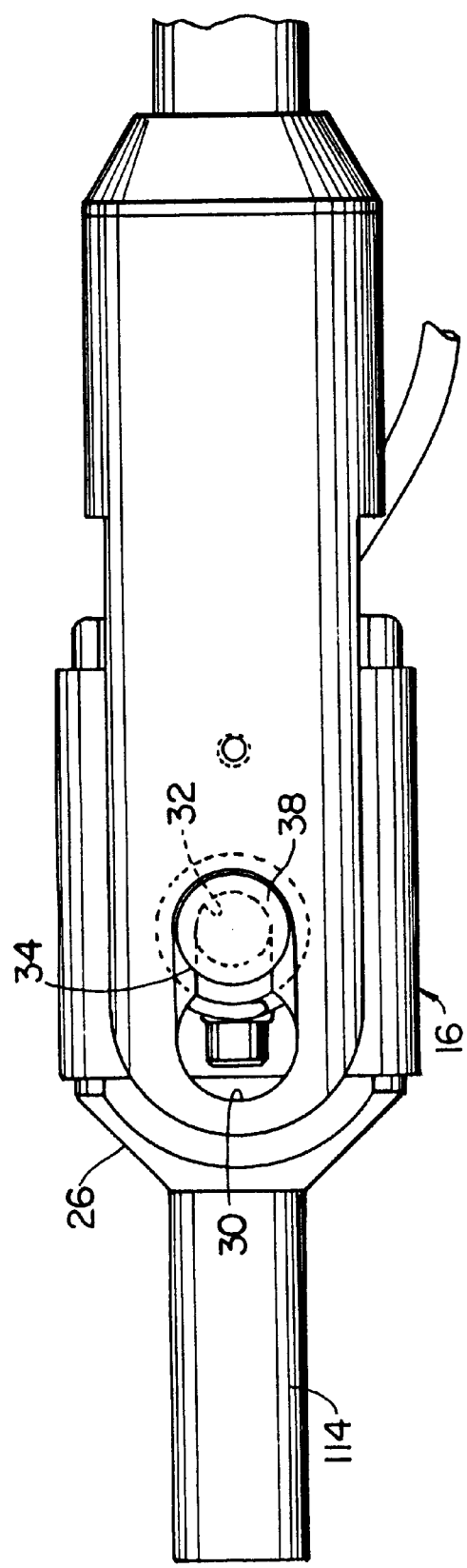
FIG. 9 is a bottom view of the distal portion of the same apparatus.

As seen best in FIGS. 2, 5, 6 and 10, a preferred method of routing operating cable 50 is a "figure 8" configuration which comprises provision of two reversing guide members 100 and 102 secured to support members 12 and 56 respectively. Both guide members have a cylindrical outer surface and have center holes to accommodate screws 104 and 106 that are screwed into threaded holes in support members 12 and 56 so as to lock the guide members in place. Preferably but not necessarily, guides 100 and 102 have peripheral flanges 108 at their outer ends to better guide cable 50. Preferably, flanges 108 protrude from guides 100 and 102 by a distance about equal to the cross-sectional diameter of cable 50. As an alternative measure, guides 100 and 102 could be free-wheeling rollers attached to supports 12 and 56. The two strands 50A, 50B on cable 50 exit the front (distal) end of shaft 2 and pass around guide 100 before reversing direction about shaft 36. The same strands exit the rear (proximal) end of shaft 2 and pass around guide 102 before reversing direction about shaft 72.

The reason for choosing this "figure 8" arrangement is made clear by considering a simpler routing of operating cable 50 wherein guide members 100 and 102 are omitted and the cable makes a single turn about shafts 36 and 72. Referring now to FIGS. 15 and 17, with such a simple routing of cable 50, the range of rotation of axle 36 (and consequently, that of the imaging device carrier 16 and imaging device 18) is limited to the angles at which the axis of screw 82 becomes substantially perpendicular to those portions of cable 50 extending from shaft 36 toward adaptor 10. One such end limit location of screw 82 is shown by broken lines in FIG. 15. With the simple configuration of FIG. 15, a total range of rotation of the imaging device no greater than approximately 210° is possible, with the strands 50A, 50B of cable 50 being more nearly parallel than converging at the limits of rotation of shaft 36. If at the limits of rotation of shaft 36 the two strands 50A, 50B of operating cable 50 were exactly parallel to each other, the total range of rotation of shaft 36 would be 180°. The same limiting effect occurs at the proximal end because of screw 84.

The approximately 210° maximum range of rotation permitted by the simpler routing arrangement represented in part by FIGS. 15 and 17 may be sufficient for many applications. However, if a still greater range of rotation is desired, the illustrated "figure 8" cable routing arrangement may be used. With the "figure 8" cable routing arrangement, the cable strands 50A and 50B are more converging as they pass from shafts 36 and 72 to guide members 100 and 102 respectively. Consequently the rotational limits of axles 36 and 72, which are determined by the perpendicularly of screws 82 and 84 to those portions of cable 50 extending between shafts 36 and 72 and guide members 100 and 102 respectively, are increased substantially, resulting in a rotation range of about 260°. To summarize, operating cable 50, in traversing the resulting "figure 8" path, causes axle portion 36 to rotate substantially further than is possible with the simpler routing represented in FIGS. 15 and 17 in either direction before screw 82 becomes perpendicular to those portions of strands 50A and 50B extending from adaptor 10 to shaft 36. In fact, in the "figure 8" routing arrangement shown in the drawings, the limits of rotation of shaft 36 are determined by engagement of the head of screw 82 with flange 108 of guide member 100. The flange serves as a hard stop for the head of screw 82, thereby stopping further like direction rotation of axle 36. However, the primary function of flange 108 is to prevent operating cable 50 from slipping off guide post 90, and a different mechanical stop could be provided to limit rotation of shaft 36. A hard stop gives the operator a tactile indication that the imaging device is in a retrograde pointing attitude.

Figure 16:
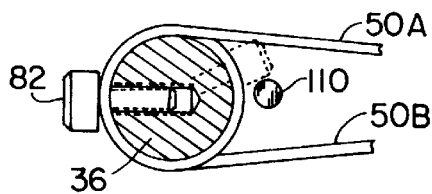
FIG. 16 is a view like FIG. 15 of an alternative embodiment of the invention.
Figure 18:
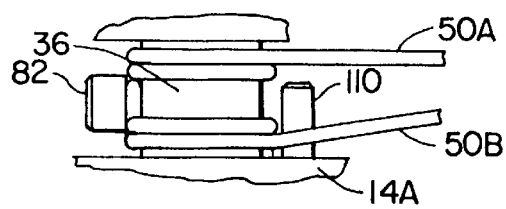
FIG. 18 is a partial side elevational view of the axle portion of the imaging device carrier shown in FIG. 16.

FIGS. 16 and 18 show a way to increase the rotational range of axle 36 without using a "figure 8" routing arrangement for cable 50. Instead, in the configuration of FIGS. 16 and 18, each of the strands 50A and 50B of operating cable 50 is wrapped more than one turn around axle 36. Thus axle 36 can be rotated more than 360°, although for practical purposes it may be advisable to limit the rotational range to just short of 360° by incorporation of a hard stop for screw 82, such as a pin 110 that is anchored in portion 14A of support member 12.

The drawings make it evident that the foregoing description of the distal end of the apparatus shown in FIGS. 1–18 applies also to the proximal end, where operating knob 70 corresponds to imaging device carrier 16. Thus the multiple-turn arrangement shown in FIGS. 16 and 18 is replicated for shaft 72.

The distal adaptor 10 is made of a material having a high coefficient of friction when mated with shaft 2 and camera support member 12, facilitating the immobility of those components with respect to each other and shaft 2 through the action of friction. Alternatively, the mutual fixation of these components can be achieved by the use of a cement or by other well known means such as pins.

Figure 14:
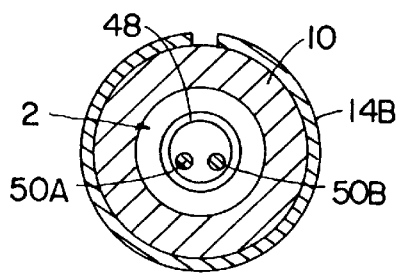
FIG. 14 is a cross-sectional view through the distal end of the shaft.

If there were excessive friction between operating cable 50 and the bore of shaft 2, and if shaft 2 were to be bent, then it might become difficult to rotate knob 70, and at the least, the operator might experience a disconcerting change in the tactile sensation of rotating knob 70. Therefore, in the preferred embodiment of the invention, shaft 2 either possesses a very low coefficient of friction with respect to operating cable 50 or is lined with a low-friction shaft liner 48 as shown in FIG. 14. In addition, distal and proximal guide posts 100 and 102 (provided they are employed) are also formed of a low friction material. In the preferred embodiment, a suitable material for these low friction components is PTFE, which is available commercially under the trademark Teflon®.

While the drawings show the operating components at the distal and proximal ends of the shaft assembly as being exposed to view, it is contemplated, at least in the case where the instrument is to function as an endoscope, that a removable shroud (not shown) may be provided to conceal guide post 100 and axle 36 and the flat portion of support member 12, and a like shroud (not shown) may be provided to conceal guide post 102 and the flat portion of support member 56. Additionally a "boot" in the form of a flexible corrugated accordion-type metal or plastic sleeve (not shown) may be disposed about spring 96 so as to conceal it from view, with one end of the sleeve embracing and being secured to collar 90 and the other end embracing and being secured to sleeve 54. The corrugations of the "boot" enable it to contract and expand longitudinally (in the manner of an accordion) as sleeve 54 moves axially toward or away from collar 90.

As a further modification, it is contemplated that rotation of axle 72 may be effected by a motive device other than by hand. The motive device (not shown) would be mounted to support member 56 and would comprise a reversible electric, pneumatic or hydraulic motor, and mechanical means coupling the output shaft of such motor to axle 72, whereby operation of the motor will cause axle 72 to turn and thereby cause a motion of operating cable 50 that results in rotation of distal axle 36 and carrier 16. In this connection, axle 72 serves as a driver means for operating cable 50, and the latter in turn functions as a motion translating or coupling means whereby axle 36 is driven in synchronism and in phase with axle 72.

If desired, rotation of carrier 16 can be recorded faithfully by a suitable readout mechanism or some position-indicating device other than marker 71, e.g., by an electronic shaft encoder (not shown) that is coupled to axle 72 (or axle 36) and drives an electronic up-down counter and display (not shown).

Extension 114 of camera housing 26 preferably has a dual tube construction, comprising inner and outer tubes (not shown) with a plurality of optical fibers (also not shown) being disposed between the two tubes for the purpose of transmitting light to the region in front of the extension. The front ends of the optical fibers terminate in a common plane at the front ends of the two tubes, while the rear ends of the fibers extend out beyond the rear or proximal ends of the two tubes and are collected in housing 26 where they are coupled to a flexible multifunction camera cable 120 having a water impervious, electrically insulating sheath. Such a dual tube construction is known, being disclosed for example, in copending U.S. patent applications Ser. No. 08/722,742, filed Oct. 1, 1996, and Ser. No. 08/748,733, filed Nov. 14, 1996, and all of the relevant information contained in said applications is included herein by reference.

Figure 19:
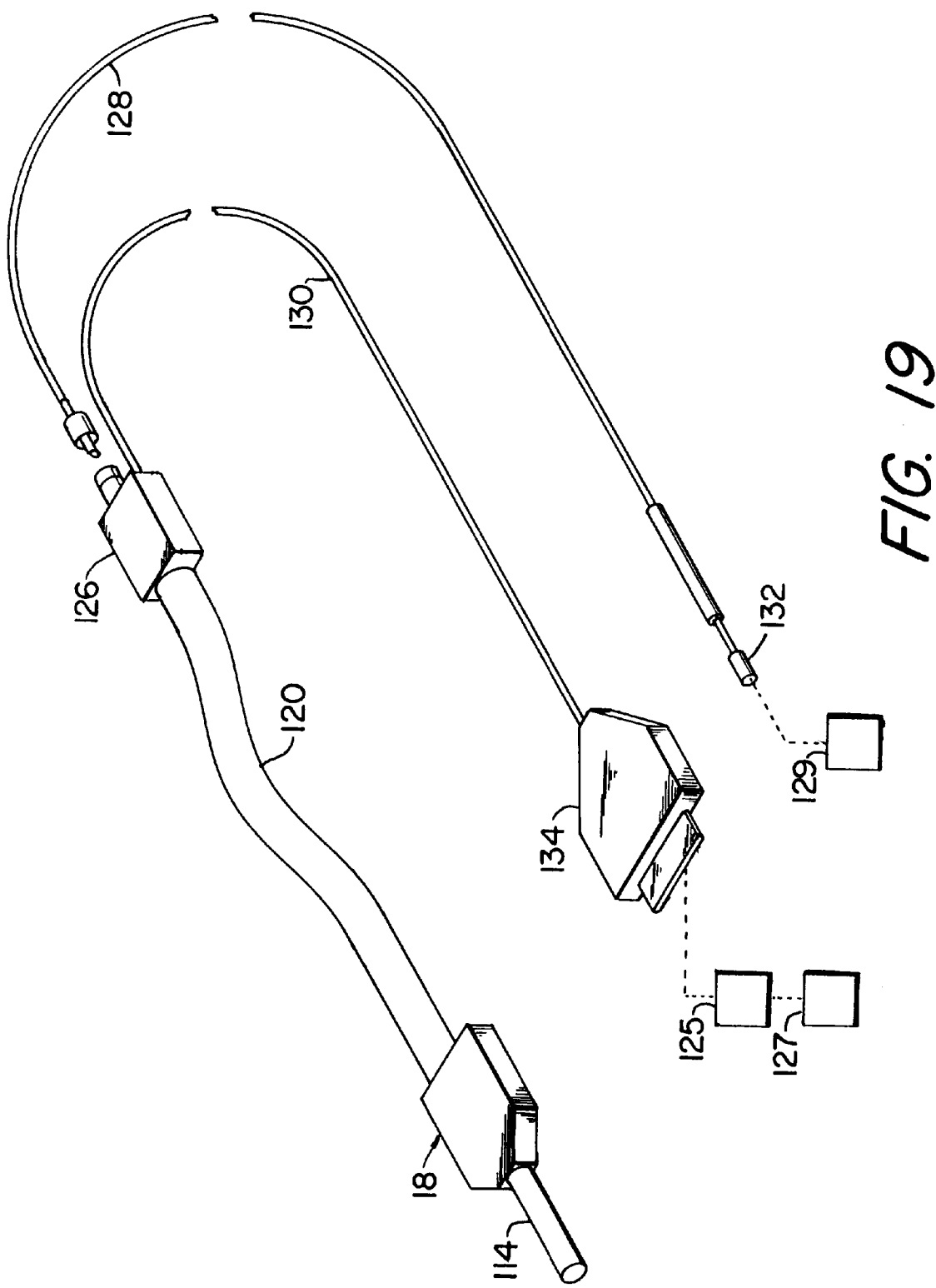
FIG. 19 illustrates a cable assembly for connecting the camera to a light source and means for processing electronic image signals produced by the camera.

Referring now to FIG. 19, camera cable 120 projects out from the proximal end of the camera housing and comprises (a) optical fibers (not shown) that are functional extensions of the optical fibers carried by extension 114 and (b) electrical conductors (also not shown) that are connected to the electronic imaging device(s) and related electronic circuit components mounted in housing 26. The outer (proximal) end of camera cable 120 is connected to a connector box 126 where the optical fibers of cable 120 are connected to a flexible light guide cable 128 of conventional construction and the electrical conductors of cable 120 are connected to a multi-conductor electrical cable 130. The proximal end of light guide cable 128 is connected to a plug-in type light guide connector 132 while the proximal end of electrical cable 128 is connected to a multi-pin plug-in type electrical connector 134. The latter connector is used to connect the electrical conductors of camera cable 124 to a video controller (represented schematically at 125) that is adapted to receive the video signals generated by the camera electronics and utilize same to generate a video image for display by a video monitor 127 or other means such as a heads-up display. The connector 132 is used to connect light guide cable 134 to a suitable light source (represented schematically at 129) whereby to provide light for illuminating the area directly in front of the camera projection 114.

Referring now to FIG. 10, camera cable 120 is shown in two ways: conventionally, in solid lines, as emanating from the proximal (rear) end of camera 18, and also unconventionally, in broken lines, as emanating from the distal (front) end of the camera which is pointing proximally (rearwardly). In the case of cameras or other imaging devices intended to be operated mostly looking in a retrograde direction, the illustrated unconventional attachment of cable 120 to the front end of camera 18 may result in less tendency for it to become entangled and may afford it a more convenient and less obtrusive path from the camera to apparatus for processing the electrical responses from the camera and a suitable light source (both not shown).

As noted previously, shaft 2 may be malleable so as to allow it to be bent to a suitable shape. By way of example, but not limitation, shaft 2 may be a malleable member having a construction as shown in co-pending U.S. application Ser. No. 08/722,742, filed Oct. 1, 1996 for "Video Endoscopes". Further by way of information, FIGS. 20–25 illustrate different ways to construct a malleable shaft for the purposes of this invention and also for other purposes. It is to be understood that the various design elements or features shown in FIGS. 20–25 can be combined in numerous permutations and combinations, all of which are to be considered as being within the scope of this Invention.

Figure 20:
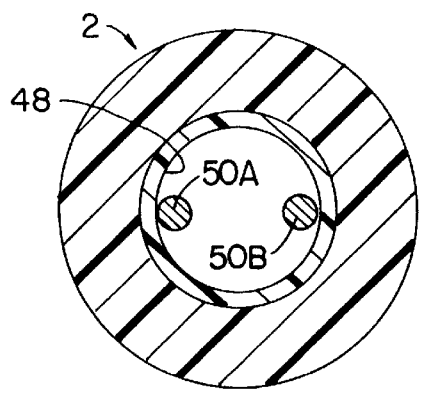
FIGS. 20–25 illustrate various ways to construct a malleable shaft for use in the present invention.

FIG. 20 is an enlarged cross-section of shaft 2 with liner 48. Shaft 2 is preferably formed from a malleable non-metallic substance such as high-density polyethylene. For purposes of this invention, a shaft or tube or rod is malleable if it can be manually bent to a desired shape and retain all or much of that shape until the user elects to bend the shaft to a different shape. The method of manufacturing a malleable polyethylene is a known technique and, therefore, does not form a novel part of the present invention. Liner 48 is made of a flexible relatively low-friction material such as PTFE so as to assure that the legs or strands 50A, 50B of cable 50 can move smoothly and with minimal effort within shaft 2.

Figure 21:
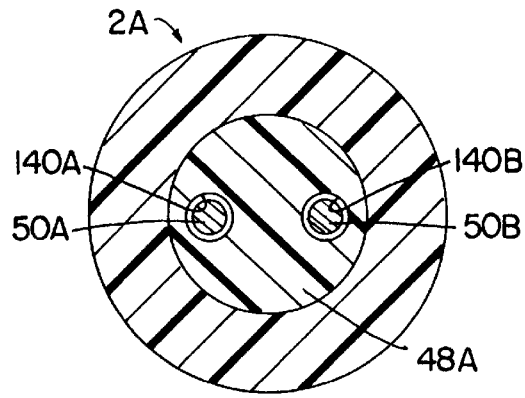

FIG. 21 shows a hollow shaft 2A made of a high density malleable polyethylene that can be bent and retain its bent shape like shaft 2. The bore of shaft 2A contains a solid liner 48A that is made of a relatively low-friction material such as PTFE and has two lumens 140A, 140B to accommodate cable legs 50A and 50B. The latter run freely in the two lumens. It is obvious that the constructions of FIGS. 20 and 21 are similar except for the form of liner which prevents cable legs 50A, 50B from contacting the relatively high-friction material of shaft 2 and 2A.

Figure 22:
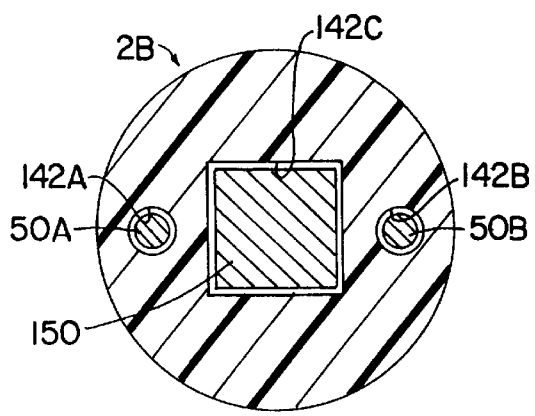

FIG. 22 illustrates in cross-section a construction in which a liner is not necessary, inasmuch as shaft 2B is made of a relatively low-friction material such as PTFE having three lumens 142A, 142B, 142C, the first two of which are smaller in cross-section and accommodate cable legs 50A, 50B, and the third lumen 142C being somewhat larger to accommodate a malleable core member 150. Since PTFE is relatively non-malleable (in the sense that although it can be bent it will not retain faithfully the shape into which it has been bent), another means for imparting malleability is necessary. Toward this end, malleable core member 150 is formed from a highly malleable metal such as annealed aluminum or lead. As a result, if shaft 2B is bent, the bend will be preserved because the propensity of shaft 2B to unbend (or spring back) will be overcome by the tendency of the higher-modulus core member 150 to maintain its bent attitude. By virtue of its cross-sectional shape, core member 150 is "keyed" to the relatively closely-fitted center lumen 142C of shaft 2B, so that when the shaft assembly, consisting of shaft 2B, cable legs 50A, 50B, and core member 150, is bent, core member 150 will not tend to rotate inside of shaft 2B. Such relative rotation might make it difficult for the user to re-bend the shaft assembly when a change of bend is desired. It should be noted that lead, having toxic properties, requires insulation from contact with body tissues and fluids during a surgical procedure. Plating and coatings on the lead metal member, and a plastic heat-shrink tube surrounding the lead metal member, are typical means for providing required insulation.

Figure 23:
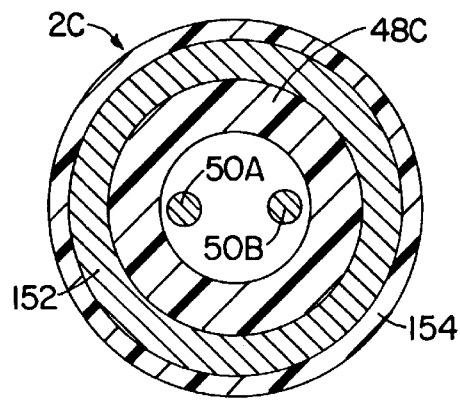

FIG. 23 shows in cross-section a shaft 2C that comprises a flexible relatively low friction liner 48C, such as a PTFE tube, in which cable legs 50A, 50B move freely. Liner 48C is encircled by a malleable tube 152, preferably formed from a malleable metal such as lead which (as noted above) must be insulated from contact with body tissues and fluids when used surgically. To provide such insulation, an outer covering 154, such as plastic heat shrink tube, may be employed.

Figure 24:
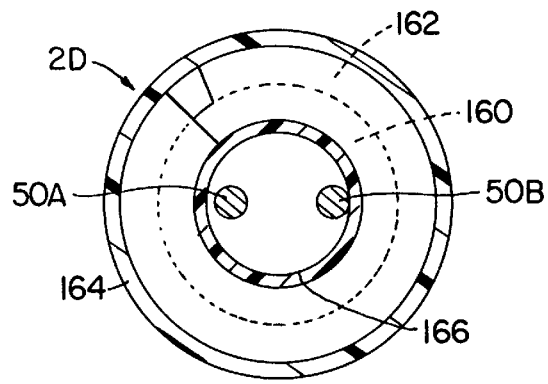
Figure 25:
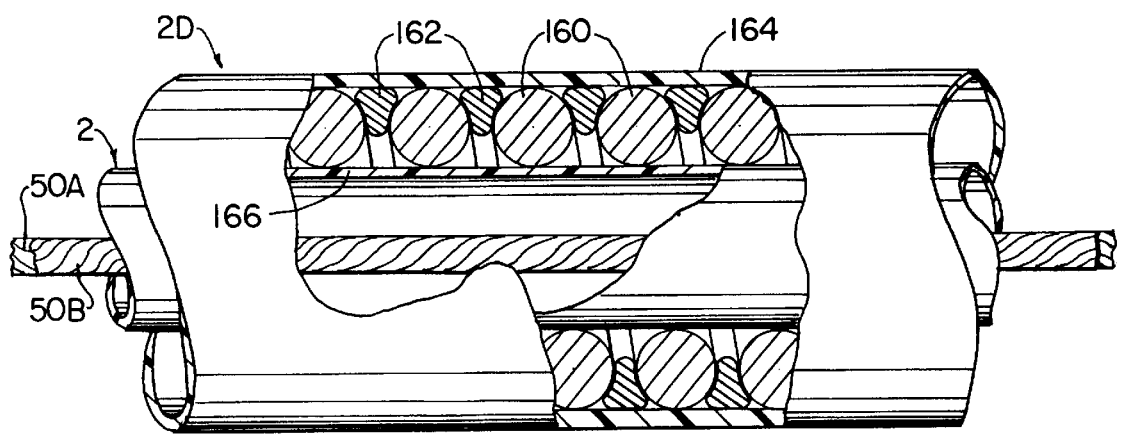

FIGS. 24 and 25 depict a malleable shaft construction known as a "gooseneck shaft," also known as a "gooseneck conduit". The gooseneck shaft may take various forms known to persons skilled in the art. (See, for example, the gooseneck constructions shown by U.S. Pat. Nos. 5,009,793, 5,033,528, 5,209,562, and 5,513,827.)

Preferably, the gooseneck shaft or conduit 2D comprises a primary helix (or helical coiled spring) 160 made of a metal wire that is substantially circular in cross-section, and a secondary helix (or helical coiled element) 162 that surrounds and is interfitted with the turns of primary helix 160. Secondary helix 162 is preferably made of a metal wire that has a generally triangular shape in cross-section, as seen in FIG. 25. The wire of secondary helix 162 may have concavities formed in its surfaces that contact the turns of primary helix 160, as shown in FIG. 25, so as to make a close fit between the two helical members. The turns of primary helix 160 are separated from their normal spacing by the turns of secondary helix 162, with the latter making a tight frictional fit with the turns of the primary helix. The result is that the two helical members cooperate to provide malleability of the gooseneck shaft. In its as-formed state the gooseneck is relatively straight. However, the foregoing construction allows the gooseneck to be bendable lengthwise (as the term "gooseneck" implies), and if the gooseneck is bent to a desired shape, the friction between the two helical members causes them to remain in that bent shape. In a preferred form, the gooseneck is completed by provision of a flexible insulating tubular outer covering or sheath 164, which preferably is made of a suitable plastic such as polyethylene and extends along the length of helical members 160 and 162. A liner 166, formed of a flexible relatively low-friction material such as PTFE, may be provided to assure free movement of cable legs 50A, 60B within the cable.

As used herein, the term "video camera" is to be construed as a device that comprises the combination of an objective lens unit and a solid state video imaging device positioned to receive images transmitted by the objective lens unit, with the imaging device being disposed in the focal plane of the objective lens unit for direct reception of images transmitted by the objective lens unit, or being optically coupled to the objective lens unit by some form of optical relay means such a rod-type lens. Also as used herein the term "video endoscope" is to be construed as an endoscope that utilizes a video camera.

The apparatus shown in FIGS. 1–19 constitutes a video endoscope in the sense that it comprises a video camera and an elongated shaft for supporting the camera. It offers the advantage that the camera and camera support member 12 may be sized so that their combined cross-sectional profile is small enough to enable the endoscope to be used for minimally invasive surgery.

Although this invention has been described and illustrated as an endoscope especially adapted for surgical procedures, the invention is not limited to endoscopic use. In this connection it is to be understood that as used herein the term "endoscope" is to be construed as including borescopes or other scopes of like or other purpose.

It is believed evident that the invention may have usefulness in various applications where remotely-controlled rotation of a device is desired. Therefore, it is contemplated that the invention may be modified and/or used in various ways obvious to persons skilled in the art from the foregoing description, with different uses possibly necessitating modification or replacement of components of the illustrated apparatus. For one thing, the size of the device supporting and steering guide may be varied, e.g., scaled up as may be required in the case of a borescope. For another thing, devices of different types can be mounted on the distal axle 36 of the illustrated apparatus in replacement of camera 18. Thus, for example, it is contemplated that camera 18 could be a digital still camera, or it could be replaced by a viewing scope that comprises a housing that is releasably attached to carrier 16, an objective lens mounted in the housing for scanning images via a window in said housing, and means including a flexible cable having two sets of optical fibers, one set for transmitting light to the areas scanned by the objective lens and the other for receiving and relaying the images collected by the objective lens to a viewing device, such as an eyepiece unit. Other devices that could be attached to carrier 16 in place of the camera are solid state surgical lasers, magnetic sensors, infra-red or other radiation sensors, infra-red or other radiation transmitters, ultrasonic transducers, surgical lasers, and other surgical instruments, e.g., surgical scissors or grasper devices. Also the shape, design and construction of carrier 16 may be varied.

It should be noted also that the steerable shaft assembly, particularly in its malleable form, may be used for other purposes or incorporated in devices other than endoscopes or like instruments. An obvious advantage of the illustrated device-steering shaft assembly is that the design of its operating mechanism and the means for maintaining tension on the operating cable connecting the two shafts 36 and 72 is such as to accommodate use of a shaft that can be bent and is capable of retaining its bent shape.

In addition to the modifications described or suggested above, it should be noted that that specific components of the steerable shaft may be modified in shape, size or material of manufacture, and that two or more components may be formed as a single component. For example, shaft 2B may be made of an elastomeric material and lumens 142A, 142B could be lined with a coating of a low friction material such as Teflon®. Also in some cases, depending on the use to which the instrument is put, screws 82 and/or 84 may be omitted. A further possible modification is to shift the automatic tensioning feature to the distal end of the instrument. In other words, the adaptor 10 could be attached to the proximal end of shaft 2 and support member 56 could be anchored to adaptor 10, while sleeve 54, collar 90 and spring 96 could be mounted to the distal end of shaft 2. Still other modifications and changes will be obvious to persons skilled in the art without departing from the principles of the invention.

We claim:

1. An instrument for viewing a surgical site comprising
   a shaft having proximal and distal ends and an internal passageway;
   a first support member attached to and projecting from said distal end of said shaft;
   a second support member attached to and projecting from said proximal end of said shaft;
   camera mounting means pivotally attached to said first support member outside of said shaft;
   a video camera carried by said camera mounting means;
   operating means for pivoting said camera mounting means relative to said support member so as to alter the viewing angle of said camera, said operating means comprising a flexible cable having first and second strands extending movably within said passageway, said first and second strands being attached to said camera mounting means outside of said shaft so that exerting a pulling force on said first strand in a predetermined direction will cause said camera mounting means to pivot in a first direction and exerting a pulling force on said second strand in a predetermined direction will cause said camera mounting means to pivot in a second direction opposite to said first direction, said operating means also including means carried by said second support member for selectively exerting a pulling force on said first and second strands whereby to cause pivotal movement of said camera mounting means and
   a camera cable connected to said camera for carrying video image signals from said camera to apparatus for processing said signals and generating a video display of the image seen by the camera.

2. An instrument according to claim 1 wherein said camera cable also comprises means for transmitting light to an object viewed by said camera.

3. An instrument for viewing a surgical site comprising:
   a malleable shaft having proximal and distal ends;
   a first support member attached to said distal end of said shaft;
   camera mounting means carried by said first support member, said camera mounting means comprising an axle rotatable mounted to said first support member;
   a video camera releasably carried by said camera mounting means;
   a second support member coupled to said proximal end of said shaft; and
   operating means for pivoting said camera mounting means relative to said first support member so as to alter the viewing angle of said camera, said operating means comprising an actuating member rotatably mounted to said second support member and a flexible cable having first and second strands that extend within said shaft and are attached to said axle and said actuating member, whereby rotational movement of said actuating member will cause a pulling force to be exerted on said first strand or said second strand according to the direction of rotation of said actuating member, and said camera mounting means is caused to rotate in a first direction in response to the pulling force exerted on said first strand and in a second opposite direction in response to the pulling force exerted on said second strand.

4. An instrument for viewing a surgical site comprising:
   a shaft having proximal and distal ends and an internal passageway, said shaft being malleable in the sense that it is shape retentive with respect to its lengthwise configuration until it is bent to a new shape, whereby said shaft may be manually reformed into a selected lengthwise configuration for access to a viewing site and is adapted to remain in such selected lengthwise configuration until it is manually moved to another configuration;
   a support member attached to one of said proximal and distal ends of said shaft;
   camera mounting means pivotally attached to said support member;
   a video camera carried by said camera mounting means; and
   operating means for pivoting said camera mounting means relative to said support member so as to alter the viewing angle of said camera, said operating means comprising a flexible cable having first and second strands extending movably within said passageway, said first and second strands being coupled to said camera mounting means so that exerting a pulling force on said first strand in a predetermined direction will cause said camera mounting means to pivot in a first direction and exerting a pulling force on said second strand in a predetermined direction will cause said camera mounting means to pivot in a second direction opposite to said first direction, said operating means also including means for selectively exerting a pulling force on said first and second strands whereby to cause pivotal movement of said camera mounting means.

5. An instrument according to claim 4 wherein said shaft comprises a rod of flexible material and a malleable metal member extending lengthwise through said rod.

6. An instrument according to claim 5 wherein said rod has two parallel lumens through which extend said first and second strands of said flexible operating cable.

7. An instrument in accordance with claim 4 wherein said shaft comprises a first helical coil member defining said internal passageway, and a second helical coil member surrounding said first helical coil member.

8. An endoscope comprising:

a shaft having proximal and distal ends;

camera mounting means;

means pivotally connecting said camera mounting means to said distal end of said shaft, with the pivot axis of said mounting means extending transversely to the longitudinal axis of said shaft;

an electronic camera releasably attached to said camera supporting means;

a flexible camera cable connected to said camera and extending outside and lengthwise of said shaft, said camera cable comprising electrical wiring for electronic image transmission; and operating means coupled to said camera mounting means for selectively pivoting said camera bidirectionally relative to said distal end of said shaft, said operating means comprising a flexible cable means connected to said camera mounting means and selectively operable means coupled to said cable means for selectively causing said cable means to exert a pivoting force on said camera mounting means in a first direction or in a second opposite direction:

said shaft being manually reformable with respect to its lengthwise configuration so that (a) it may be bent to a selected shape to facilitate access to a surgical site and (b) is adapted to remain in said selected shape until manually reformed to another shape.

9. A viewing instrument comprising:

a shaft having proximal and distal ends, said shaft comprising a tubular structure that is malleable in the sense that it is shape retentive with respect to its lengthwise configuration until it is bent to a new shape, whereby said shaft may be manually reformed into a selected lengthwise configuration for access to a viewing site and is adapted to remain in such selected lengthwise configuration until manually moved to another configuration;

a viewing device support attached to said distal end of said shaft;

viewing device mounting means pivotally attached to said support;

a viewing device releasably attached to said viewing device mounting means; and operating means for pivoting said viewing device mounting means on said viewing device support, whereby to move said viewing device so as to change the viewing angle of said viewing device, said operating means comprising driver means mounted to said proximal end of said shaft, and motion translating means connecting said driver means and said viewing device mounting means, at least a portion of said motion translating means extending within said shaft.

10. An instrument in accordance with claim 9 further including a support member attached to the proximal end of said shaft, and further wherein said viewing device mounting means comprises an axle rotatably mounted to said viewing device support, said driver means comprises a rotatable member carried by said support member, and said motion translating means comprises a flexible cable having first and second strands extending between and connected to said axle and said rotatable member so that movement of said rotatable member will cause said cable strands to rotate said axle and thereby produce pivotal movement of said viewing device mounting means and said viewing device relative to said shaft.

11. An instrument in accordance with claim 9 wherein said viewing device is a video camera.

12. An instrument in accordance with claim 11 further including:

a camera cable disposed outside of said shaft, said camera cable having first and second ends with said first end being attached to said camera, said camera cable including a plurality of electrical conductors for transmission of electronic signals produced by said camera that are representative of the optical image sensed by said camera, and a plurality of optical fibers for transmitting light to a site viewed by said video camera; and means attached to said second end of said camera cable for (a) connecting said electrical conductors to means for processing the electronic signals generated by said camera and (b) connecting said optical fibers to a light source.

13. An endoscope comprising:

a video camera;

a shaft having proximal and distal ends;

a support member attached to said distal end of said shaft;

a camera carrier with said camera releasably attached to said camera carrier, said camera carrier being pivotally attached to said support member by a first pivot shaft that is rotatably coupled to said support member; and camera-pivoting means for pivoting said camera carrier so as to alter the viewing angle of said camera, said camera-pivoting means comprising a second pivot shaft that is rotatably attached to said proximal end of said shaft, means for rotating said second pivot shaft, and a motion translating means coupled to said first and second pivot shafts for causing rotational movement of said first pivot shaft in response to and in synchronism with rotational movement of said second pivot shaft, said motion translating means comprising a flexible operating cable that extends through at least one lumen in said shaft and embraces and is pinned to said first and second pivot shafts.

14. An endoscope according to claim 13 further including a first guide member carried by said support member and disposed adjacent to said first pivot shaft, and further wherein said operating cable is arranged in a figure 8 configuration about said first pivot shaft and said guide member.

15. An endoscope according to claim 14 further including a second support member attached to said proximal end of said shaft and a second guide member carried by said second support member and disposed adjacent to said second pivot shaft, and further wherein said operating cable is arranged in a figure 8 configuration about said second guide member and said second pivot shaft.

16. An endoscope according to claim 13 further including manually operable means for rotating said second pivot shaft clockwise or counterclockwise.

17. An endoscope according to claim 13 wherein said operating cable makes more than one turn about at least one of said pivot shafts.

18. An instrument comprising:

a shaft having first and second opposite ends and an internal passageway extending between said first and second ends;

first and second support means attached to and projecting from said first and second ends respectively of said shaft;

first and second axles releasably connected to said first and second support means, said axles extending transversely to the longitudinal axis of said shaft and being rotatable on their own axes relative to said support means, at least said first axle being located outside of said shaft;

an imaging device carrier attached to said first axle so as to rotate therewith;

means attached to said second axle for rotating said second axle on its own axis; and a loop of a flexible, stretch-resistant operating cable extending about and between said first and second axles, with portions of said cable extending within said passageway, said loop being movable in response to rotation of said second axle and being capable of causing said first axle to rotate in response to rotation of said second axle, said cable being under tension, and said first and second axles are releasably maintained in connection with said first and second support means respectively by a restraining force exerted thereon by said cable as a result of said tension.

19. An instrument according to claim 18 wherein said second support means is slidable lengthwise relative to said shaft, and further including spring means urging said second support means in a direction to maintain tension in said cable.

20. An instrument according to claim 19 wherein said cable undergoes a figure 8 routing at each of said first and second axles.

21. An instrument according to claim 20 wherein said shaft has at last one internal passageway extending between said first and second ends thereof, and further wherein said cable passes through said at least one internal passageway between said first and second axles.

22. An instrument according to claim 19 wherein said shaft said shaft is malleable in the sense that it is shape retentive with respect to its lengthwise configuration until it is bent to a new shape, whereby said shaft may be manually formed into a selected lengthwise configuration and is adapted to remain in such selected lengthwise configuration until it is manually reformed to another configuration.

23. An instrument according to claim 18 wherein said cable undergoes a figure 8 routing at each of said first and second axles.

24. An instrument comprising:

a shaft having proximal and distal ends;

first and second support members attached to and projecting away from said distal and proximal ends respectively of said shaft;

camera mounting means rotatably mounted to said first support member, said camera mounting means comprising a supporting axle that is rotatably attached to said first support member and a pair of mutually spaced resilient side walls for embracing and releasably gripping a video camera;

a video camera comprising a housing containing (a) an optical system for capturing optical images of objects and (b) electronic imaging means for producing video image signals representative of the optical images captured by said optical system, said camera also comprising a cable attached to said housing and coupled to said electronic imaging means for carrying said video image signals to apparatus exterior of said instrument for processing said signals and generating a video display of the optical images captured by said optical system, and said housing being disposed between and gripped by said resilient side walls and all of said cable being disposed outside of said shaft; and operating means for rotating said camera mounting means relative to said first support member so as to alter the viewing angle of said camera, said operating means comprising a flexible cable having first and second strands extending movably within said shaft, said first and second strands being coupled to said axle so that exerting a pulling force on said first strand in a predetermined direction will cause said camera mounting means to rotate in a first direction and exerting a pulling force on said second strand in a predetermined direction will cause said camera mounting means to rotate in a second direction opposite to said first direction, said operating means also including force-applying means rotatably mounted to said second support member for selectively exerting a pulling force on said first strand or said second strand whereby to cause rotational movement of said camera mounting means in a first direction or a second opposite direction.

25. An instrument according to claim 24 wherein said camera mounting means and said force-applying means are releasably mounted to said first and second support means respectively.

* * * * *

UNITED STATES PATENT AND TRADEMARK OFFICE
CERTIFICATE OF CORRECTION

PATENT NO. : 5,989,182
DATED : November 23, 1999
INVENTOR(S) : Koichiro Hori et al.

It is certified that error appears in the above-indentified patent and that said Letters Patent is hereby corrected as shown below:

Claim 22, column 19, second last line, delete "said shaft".

Signed and Sealed this

Thirtieth Day of May, 2000

Attest:

Q. TODD DICKINSON

*Attesting Officer*     *Director of Patents and Trademarks*